US00PP10080P

United States Patent [19]

Meier et al.

[11] Patent Number: Plant 10,080

[45] Date of Patent: Oct. 21, 1997

[54] 'BA 77 700' KENTUCKY BLUEGRASS

[75] Inventors: Virgil D. Meier; Eugene W. Mayer, both of Marysville, Ohio; J. Kevin Turner, Salem, Oreg.

[73] Assignee: OMS Investments, Inc., Wilmington, Del.

[21] Appl. No.: 680,167

[22] Filed: Jul. 15, 1996

[51] Int. Cl.[6] ..... A01H 5/00

[52] U.S. Cl. ..... Plt./90.2

[58] Field of Search ..... Plt./90.2

[56] References Cited

U.S. PATENT DOCUMENTS

| | | | |
|---|---|---|---|
| P.P. 3,156 | 5/1972 | Fuchigami et al. | Plt./902 |
| P.P. 3,186 | 5/1972 | Barenbrug et al. | Plt./90.2 |
| P.P. 4,336 | 11/1978 | Mayer et al. | Plt./90.2 |
| P.P. 6,280 | 9/1988 | Meier et al. | Plt./90.2 |
| P.P. 6,537 | 1/1989 | Meier et al. | Plt./90.2 |
| P.P. 6,538 | 1/1989 | Meier et al. | Plt./90.2 |
| P.P. 6,585 | 2/1989 | Meier et al. | Plt./90.2 |
| P.P. 7,831 | 3/1992 | Meier et al. | Plt./90.2 |
| P.P. 8,490 | 12/1993 | Meier et al. | Plt./90.2 |
| P.P. 9,036 | 1/1995 | Meier et al. | Plt./90.2 |
| P.P. 9,209 | 7/1995 | Meier et al. | Plt./90.2 |
| P.P. 9,611 | 7/1996 | Meier et al. | Plt./90.2 |
| P.P. 9,848 | 4/1997 | Meier et al. | Plt./90.2 |

*Primary Examiner*—James R. Feyrer

*Attorney, Agent, or Firm*—Jones, Day, Reavis & Pogue

[57] ABSTRACT

A variety of Kentucky Bluegrass having a medium to high level of resistance to a broad spectrum of serious diseases, including leaf spot, dollar spot, rusts, and necrotic ring spot; an attractive green color throughout the growing season; good early spring greening; medium to high quality turf formation under a wide variety of environmental conditions; a moderately wide blade; and a high level of seed yielding capacity.

1 Drawing Sheet

BACKGROUND OF THE INVENTION

1. Field of the Invention

The present invention relates to a new and distinct variety of *Poa pretensis* that has been designated Ba 77-700 Kentucky Bluegrass.

2. Description of Related Art

Kentucky Bluegrasses have been disclosed in U.S. Plant Pat. No. 3,156, issued May 9, 1972; U.S. Plant Pat. No. 3,186, issued May 23, 1972; U.S. Plant Pat. No. 4,336, issued Nov. 28, 1978; U.S. Plant Pat. No. 6,280, issued Sep. 6, 1988; U.S. Plant Pat. Nos. 6,537 and 6,538, issued on Jan. 17, 1989; U.S. Plant Pat. No. 6,585, issued Feb. 7, 1989; U.S. Plant Pat. No. 7,831, issued Mar. 17, 1992; U.S. Plant Pat. No. 8,490, issued Dec. 7, 1993; U.S. Plant Pat. No. 9,036, issued Jan. 3, 1995; U.S. Plant Pat. No. 9,209 issued Jul. 18, 1995; and pending U.S. plant pataent application Ser. No. 08/453,864, filed May 30, 1995 now U.S. Plant Pat. No. 9,611, Ser. No. 08/532,995, filed Sep. 22, 1995, now U.S. Plant Pat. No. 9,848 and Ser. No. 08/604,763 filed Feb. 23, 1996, as well as U.S. plant patent application Ser. No. 08/680,168, filed coextensively herewith.

SUMMARY OF THE VARIETY

Ba 77-700 plant material was selected from an old turf area on a farmstead in Union County, Ohio. After testing and observing this variety, it was determined to be a distinct variety, and it was asexually propagated by rhizomes, tillers and disseminules.

Seed of Ba 77-700 Kentucky Bluegrass was produced first at Marysville, Ohio and later at Gervais, Oreg. This seed was used to plant turf performance evaluation trials and later seed production fields. Asexual production of Ba 77-700 by propagules (tillers and rhizomes) and by disseminules (modified caryopses produced by apomixis) has consistently produced progeny plants indistinguishable from the mother plant. The apomixis level of Ba 77-700 is approximately 95% based upon examining seedling characteristics of approximately 100 to 150 seedlings from different crop years in a growth chamber.

Ba 77-700 has a number of highly desirable characteristics including a medium to high level of resistance to Drechslera spp. that causes leaf spot, melting out and crown rot, Puccinia spp. that causes several types of rust infections, *Schlerotinia homoeocarpa* that causes dollar spot and *Leptosphaeria korrae* that causes necrotic ring spot. Ba 77-700 has an attractive leafy turf type growth habit; moderately wide leaf blades and an attractive dark green color which can be maintained throughout the entire growing season. Ba 77-700 demonstrates good early spring greening and winter color under mild winter conditions. Ba 77-700 is an overall good turfgrass performer as evidenced by medium to high scores for quality and color. Ba 77-700 has a high seed yield potential in the bluegrass seed production region of the northwestern United States.

In comparison with a number of other Kentucky Bluegrass varieties, Ba 77-700 seed is above average in length; and is average in width and rachilla length. The panicle is average in length; below average in width and whorl numbers and above average in branch numbers for both the lower and third whorls. Ba 77-700 has average size spikelets and glumes and below average number of florets. The peduncle is significantly longer and wider than many other grasses. The culm and top internode are of average length but the number of nodes on the culm are significantly lower.

Ba 77-700 has a flag leaf that is average in length, above average in width and significantly thicker than many other Kentucky Bluegrass varieties. The ligule and leaf margin hair are significantly longer and more abundant than many other Kentucky Bluegrass varieties. The vegetative leaf is average in length and width but above average in thickness. The ligule of the vegetative leaf is significantly shorter than many other grasses and the sheath color is above average.

Figure 1:
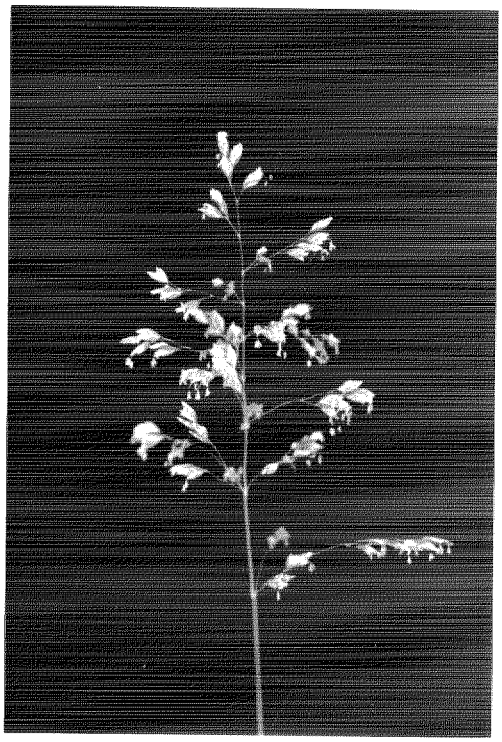
FIG. 1 is a Ba 77-700 Kentucky Bluegrass panicle.
Figure 2:
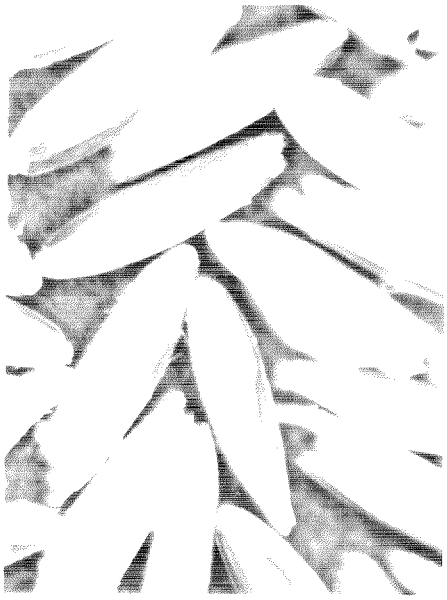
FIG. 2 is a Ba 77-700 Kentucky Bluegrass seed.
Figure 3:
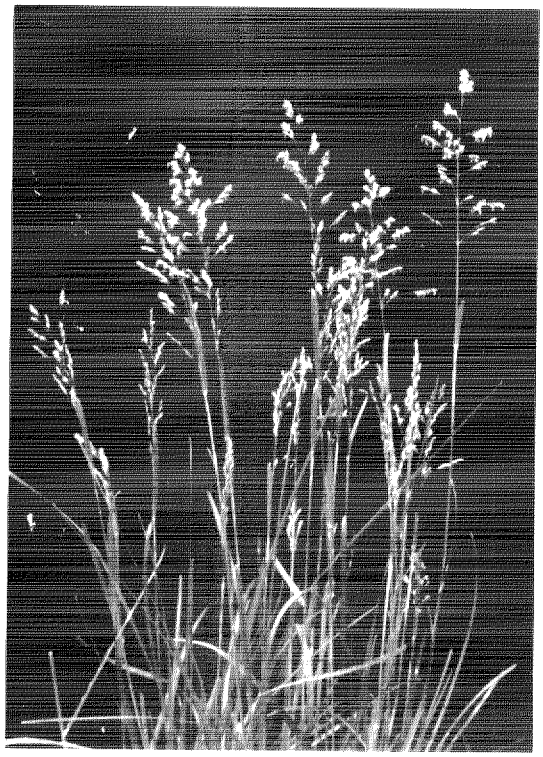
FIG. 3 is a Ba 77-700 Kentucky Bluegrass plant during anthesis.

DETAILED DESCRIPTION OF THE VARIETY 77-700 Kentucky Bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60°–80° F.), culms are erect averaging 39.7 cm in length and 2.9 nodes per culm and the uppermost internode averages 9.7 cm in length. The peduncle averages 26.9 cm in length and 0.82 mm in width. The leaf averages 4.3 cm in length, 3.7 mm in width and 0.22 mm in thickness and the ligule 1.3 mm in length. The vegetative leaf averages 18.6 cm in length, 3.8 mm in width, 0.341 mm in thickness and a ligule length of 0.21 min.

The panicle averages 77.5 mm in length, 56.1 mm in width, and 8.7 whorls. The lowest whorl averages 4.0 branches and the third whorl from the bottom of the panicle averages 3.5 branches. A spikelet in the lowest whorl averages 4.6 mm in length, 2.4 mm in width, 3.3 florets and the outer glume and inner glume average 2.7 and 3.3 mm in length, respectively. A spikelet from the third whorl from the bottom of the panicle averages 4.8 mm in length, 2.6 mm in width, 3.4 florets, and the outer glume and inner glume averages 2.8 and 3.3 mm in length, respectively.

After the seed has been conditioned, the lemma has a generally smooth keel with occasional short hairs and a few long fine hairs at the base. The conditioned seed of Ba 77-700 averages 3.05 mm in length, 0.88 mm in width, a rachilla length of 0.82 mm and an average quantity of lemma hairs. The seed count for Ba 77-700 averages approximately 1,065,922 seeds per pound.

Comparisons of Ba 77-700 with other Kentucky Bluegrass varieties in terms of seed numbers per pound are shown in Table 1 as follows:

TABLE 1

Comparison of Seed Numbers Per Pound of Ba 77-700 and Other Kentucky Bluegrass Varieties at Marysville, OH After Conditioning

| Variety | Seeds Per Pound |
|---|---|
| Ba77-700 | 1,065,992 |
| Abbey | 1,003,037 |
| Adelphi | 1,383,976 |
| Allure | 1,359,914 |
| America | 1,659,824 |
| Ascot | 1,039,000 |
| Baron | 1,051,693 |
| Bristol | 1,270,821 |
| Buckingham | 978,000 |
| Cannon | 1,171,000 |
| Chateau | 1,300,105 |
| Coventry | 1,246,200 |
| Eclipse | 1,335,668 |
| Fairfax | 1,250,997 |
| Georgetown | 1,431,000 |
| Gnome | 1,017,641 |
| Kelly | 921,166 |
| Marquis | 1,054,642 |
| Midnight | 1,227,000 |
| Nassau | 1,127,130 |
| Ram I | 1,214,000 |
| Touchdown | 1,211,000 |
| Victa | 1,038,298 |
| Viva | 1,025,586 |

Ba 77-700 differs significantly morphologically from many other Kentucky Bluegrass varieties in regard to the following characteristics: (1) peduncle length and width; (2) culm nodes; (3) flag leaf thickness, ligule length and leaf margin hairs and (4) vegetative leaf ligule length.

Since environmental conditions such as soil and climate may influence morphological characteristics to some extent, comparisons of morphological characteristics of Ba 77-700 were made with other Kentucky Bluegrass varieties under like conditions and the comparisons are set forth in the following Tables 2–10:

TABLE 2

Morphological Comparison of Seed and Rachilla Measurements and Lemma Hair of Ba 77-700 and Other Kentucky Bluegrass Varieties at Marysville, OH After Conditioning

| | Seed | | | |
|---|---|---|---|---|
| Variety | Length mm | Width mm | Rachilla mm | Lemma* Hair |
| Ba 77-700 | 3.05 | 0.88 | 0.82 | 3.8 |
| Abbey | 2.97 | 0.89 | 0.80 | 3.8 |
| Adelphi | 2.70 | 0.84 | 0.65 | 4.4 |
| Allure | 2.78 | 0.86 | 0.70 | 4.7 |
| America | 2.40 | 0.68 | 0.68 | 2.8 |
| Ascot | 2.99 | 0.85 | 0.82 | 3.9 |
| Baron | 3.08 | 0.81 | 0.71 | 5.0 |
| Bristol | 2.94 | 0.88 | 0.73 | 4.3 |
| Buckingham | 3.23 | 0.89 | 0.88 | 4.2 |
| Cannon | 3.00 | 0.94 | 0.86 | 4.9 |
| Chateau | 2.81 | 0.86 | 0.71 | 4.5 |
| Coventry | 2.71 | 0.81 | 0.70 | 4.0 |
| Eclipse | 2.77 | 0.83 | 0.68 | 3.5 |
| Fairfax | 2.77 | 0.89 | 0.68 | 4.4 |
| Georgetown | 2.94 | 0.82 | 0.74 | 4.9 |
| Gnome | 2.78 | 0.83 | 0.75 | 4.1 |
| Kelly | 3.07 | 0.89 | 0.75 | 4.2 |
| Marquis | 2.97 | 0.87 | 0.83 | 4.7 |
| Midnight | 2.94 | 0.76 | 0.78 | 5.7 |
| Nassau | 3.07 | 0.86 | 0.68 | 3.4 |
| Ram I | 3.23 | 0.89 | 0.80 | 6.0 |
| Touchdown | 2.93 | 0.88 | 0.71 | 4.6 |
| Victa | 3.00 | 0.80 | 0.82 | 3.5 |
| Viva | 3.04 | 0.91 | 0.80 | 4.4 |
| LSD (.05) | 0.16 | 0.05 | 0.13 | 0.86 |

*Rating Scale: 0–9; 9 = longest row of hairs

TABLE 3

Morphological Comparison of Panicles, Whorl Number and Whorl Branches of Ba 77-279 and Other Kentucky Bluegrass Varieties in the Greenhouse at Marysville, OH

| | Panicles | | | | Number of Branches | |
|---|---|---|---|---|---|---|
| Variety | Nodding* | Length mm | Width mm | Whorl Number | Lowest Whorl | Third Whorl |
| Ba 77-700 | 1.2 | 77.5 | 56.1 | 8.7 | 4.0 | 3.5 |
| Abbey | 1.6 | 80.4 | 59.3 | 9.3 | 3.8 | 3.3 |
| Adelphi | 1.8 | 106.8 | 76.4 | 10.0 | 3.6 | 3.0 |
| Allure | 2.2 | 60.8 | 47.6 | 8.4 | 3.9 | 3.0 |
| America | 2.3 | 67.7 | 51.1 | 8.8 | 3.3 | 3.5 |
| Ascot | 2.4 | 77.1 | 66.0 | 9.2 | 2.3 | 2.1 |
| Baron | 2.2 | 92.6 | 71.0 | 10.0 | 3.4 | 2.8 |
| Bristol | 2.0 | 85.5 | 61.5 | 8.4 | 2.8 | 2.7 |
| Buckingham | 2.0 | 88.8 | 62.0 | 9.3 | 2.1 | 2.1 |
| Cannon | 1.1 | 80.2 | 55.3 | 9.8 | 4.1 | 3.9 |
| Chateau | 2.9 | 65.2 | 57.3 | 8.5 | 3.3 | 2.8 |
| Coventry | 2.5 | 64.0 | 54.2 | 8.4 | 3.3 | 2.5 |
| Eclipse | 1.3 | 89.2 | 74.0 | 10.7 | 3.3 | 2.1 |
| Fairfax | 1.5 | 67.4 | 46.6 | 8.8 | 3.3 | 3.1 |

TABLE 3-continued

Morphological Comparison of Panicles, Whorl Number and Whorl Branches of Ba 77-279 and Other Kentucky Bluegrass Varieties in the Greenhouse at Marysville, OH

| | Panicles | | | | Number of Branches | |
|---|---|---|---|---|---|---|
| Variety | Nodding* | Length mm | Width mm | Whorl Number | Lowest Whorl | Third Whorl |
| Georgetown | 1.0 | 80.0 | 57.0 | 7.4 | 2.1 | 2.6 |
| Gnome | 1.1 | 80.6 | 56.0 | 10.6 | 4.6 | 3.9 |
| Kelly | 2.0 | 88.0 | 70.2 | 9.8 | 4.6 | 3.7 |
| Marquis | 1.1 | 82.0 | 63.0 | 10.3 | 3.9 | 3.6 |
| Midnight | 2.0 | 75.8 | 48.4 | 7.1 | 2.9 | 3.0 |
| Nassau | 2.2 | 91.2 | 68.6 | 10.0 | 2.5 | 2.1 |
| Ram I | 1.3 | 67.7 | 47.0 | 7.3 | 3.0 | 3.2 |
| Touchdown | 1.1 | 73.1 | 75.0 | 7.6 | 2.1 | 2.3 |
| Victa | 1.7 | 74.9 | 58.3 | 10.0 | 4.7 | 3.5 |
| Viva | 1.6 | 88.8 | 68.4 | 8.8 | 4.3 | 3.7 |
| LSD (.05) | 0.68 | 7.35 | 8.62 | 0.66 | 0.72 | 0.50 |

*Rate Scale: 1–9; 9 = most nodding

TABLE 4

Morphological Comparison of Spikelets and Florets of Ba 77-700 and Other Kentucky Bluegrass Varieties in the Greenhouse at Marysville, OH

| | Spikelet* | | | | Number of Florets | |
|---|---|---|---|---|---|---|
| | Lowest Whorl | | Third Whorl | | Per Spikelet | |
| Variety | Length mm | Width mm | Length mm | Width mm | Lowest Whorl | Third Whorl |
| Ba 77-700 | 4.6 | 2.4 | 4.8 | 2.6 | 3.3 | 3.4 |
| Abbey | 4.4 | 2.2 | 4.5 | 2.2 | 3.0 | 3.0 |
| Adelphi | 4.6 | 2.2 | 4.8 | 2.2 | 4.4 | 4.4 |
| Allure | 4.3 | 2.2 | 4.3 | 2.2 | 3.4 | 3.2 |
| America | 4.6 | 2.2 | 4.4 | 2.3 | 4.5 | 4.3 |
| Ascot | 5.4 | 2.6 | 5.3 | 2.9 | 3.1 | 3.1 |
| Baron | 5.4 | 2.8 | 5.4 | 3.1 | 4.0 | 4.2 |
| Bristol | 4.9 | 2.4 | 5.0 | 2.5 | 4.2 | 4.5 |
| Buckingham | 5.6 | 3.2 | 5.6 | 3.3 | 4.1 | 4.1 |
| Cannon | 4.7 | 2.4 | 4.6 | 2.6 | 2.7 | 2.7 |
| Chateau | 4.4 | 2.4 | 4.4 | 2.4 | 3.4 | 3.5 |
| Coventry | 4.4 | 2.2 | 4.5 | 2.4 | 3.2 | 3.5 |
| Eclipse | 4.6 | 2.4 | 4.6 | 2.4 | 3.6 | 3.6 |
| Fairfax | 4.6 | 2.3 | 4.7 | 2.4 | 3.2 | 3.3 |
| Georgetown | 5.0 | 2.3 | 5.0 | 2.6 | 4.8 | 4.9 |
| Gnome | 4.6 | 2.5 | 4.6 | 2.9 | 3.2 | 3.2 |
| Kelly | 5.1 | 2.5 | 5.2 | 2.8 | 3.7 | 3.8 |
| Marquis | 4.3 | 2.2 | 4.4 | 2.3 | 3.1 | 2.9 |
| Midnight | 5.3 | 2.5 | 5.5 | 2.4 | 4.4 | 4.7 |
| Nassau | 4.7 | 2.6 | 4.8 | 3.0 | 4.2 | 4.3 |
| Ram I | 5.4 | 2.6 | 5.3 | 2.8 | 3.6 | 3.4 |
| Touchdown | 5.1 | 2.9 | 4.8 | 2.8 | 4.1 | 4.0 |
| Victa | 4.5 | 2.5 | 4.5 | 2.4 | 3.3 | 3.2 |
| Viva | 4.6 | 2.5 | 4.7 | 2.6 | 2.6 | 2.8 |
| LSD (.05) | 0.41 | 0.35 | 0.38 | 0.35 | 0.58 | 0.53 |

*Microscope measurements

TABLE 5

Morphological Comparison of Glumes of Ba 77-700 and Other Kentucky Bluegrass Varieties in the Greenhouse at Marysville, OH

| | Glume Length (mm) | | | | Glume Hairs* | | | |
|---|---|---|---|---|---|---|---|---|
| | Outer | | Inner | | Lowest Whorl | | Third Whorl | |
| Variety | Lowest Whorl | Third Whorl | Lowest Whorl | Third Whorl | Outer | Inner | Outer | Inner |
| Ba 77-700 | 2.7 | 2.8 | 3.3 | 3.3 | 2.4 | 2.2 | 1.9 | 2.1 |
| Abbey | 2.7 | 2.7 | 3.1 | 3.1 | 0.6 | 0.9 | 1.0 | 1.0 |
| Adelphi | 2.7 | 2.6 | 3.0 | 3.1 | 0.6 | 2.7 | 1.1 | 1.9 |
| Allure | 2.6 | 2.7 | 3.0 | 3.0 | 2.5 | 3.0 | 2.5 | 2.5 |
| America | 2.1 | 2.1 | 2.5 | 2.5 | 0.2 | 0.5 | 0.3 | 0.3 |
| Ascot | 3.7 | 3.7 | 4.1 | 4.0 | 2.1 | 3.0 | 2.0 | 2.3 |
| Baron | 3.1 | 3.2 | 3.6 | 3.7 | 4.8 | 4.4 | 4.2 | 4.6 |
| Bristol | 2.8 | 3.0 | 3.3 | 3.4 | 1.0 | 2.2 | 0.8 | 2.2 |
| Buckingham | 3.5 | 3.3 | 3.9 | 3.8 | 2.6 | 3.2 | 2.2 | 2.8 |
| Cannon | 2.8 | 2.9 | 3.2 | 3.1 | 1.7 | 2.3 | 2.1 | 2.3 |
| Chateau | 2.8 | 2.9 | 3.1 | 3.2 | 1.6 | 2.6 | 2.0 | 1.8 |
| Coventry | 2.7 | 2.8 | 3.1 | 3.1 | 1.5 | 2.7 | 1.6 | 2.4 |
| Eclipse | 3.0 | 3.0 | 3.4 | 3.4 | 1.5 | 1.9 | 1.8 | 1.9 |
| Fairfax | 2.8 | 2.9 | 3.1 | 3.2 | 2.2 | 2.2 | 2.1 | 3.1 |
| Georgetown | 2.8 | 2.8 | 3.1 | 3.1 | 1.7 | 2.7 | 1.2 | 2.5 |
| Gnome | 2.8 | 2.9 | 3.3 | 3.3 | 1.0 | 1.9 | 1.2 | 1.6 |
| Kelly | 3.0 | 3.1 | 3.4 | 3.5 | 1.3 | 1.5 | 1.1 | 0.8 |
| Marquis | 2.8 | 2.7 | 3.1 | 3.1 | 0.9 | 1.1 | 1.7 | 1.8 |
| Midnight | 2.6 | 2.6 | 3.0 | 3.1 | 1.8 | 2.8 | 1.0 | 2.4 |
| Nassau | 2.6 | 2.7 | 2.9 | 3.0 | 2.1 | 2.6 | 4.2 | 4.4 |
| Ram I | 2.9 | 3.0 | 3.6 | 3.5 | 1.1 | 2.3 | 0.7 | 1.2 |
| Touchdown | 3.3 | 3.3 | 3.8 | 3.8 | 0.7 | 2.1 | 1.1 | 1.4 |
| Victa | 2.8 | 2.7 | 3.1 | 3.1 | 0.8 | 1.1 | 1.1 | 1.3 |
| Viva | 2.8 | 2.8 | 3.2 | 3.1 | 1.7 | 1.3 | 1.3 | 2.0 |
| LSD (.05) | 0.23 | 0.22 | 0.22 | 0.23 | 0.9 | 0.9 | 0.9 | 0.9 |

*Ratings Scale: 0–9; 9 - most hairs

TABLE 6

Morphological Comparison of Flag Leaves of Ba 77-700 and Other Kentucky Bluegrass Varieties in the Greenhouse at Marysville, OH

| Variety | Length cm | Width mm | Thickness mm | Leaf Angle[1/] | Leaf Curve[2/] |
|---|---|---|---|---|---|
| Ba 77-700 | 4.3 | 3.7 | 0.22 | 2.0 | 4.6 |
| Abbey | 3.8 | 3.4 | 0.14 | 2.7 | 4.1 |
| Adelphi | 5.7 | 3.4 | 0.18 | 5.2 | 5.0 |
| Allure | 3.8 | 2.9 | 0.21 | 1.0 | 4.9 |
| America | 4.3 | 2.6 | 0.21 | 4.6 | 5.0 |
| Ascot | 4.7 | 3.5 | 0.29 | 2.1 | 4.5 |
| Baron | 7.0 | 4.2 | 0.15 | 9.2 | 4.4 |
| Bristol | 4.3 | 3.2 | 0.21 | 2.3 | 5.0 |
| Buckingham | 5.3 | 3.4 | 0.23 | 1.4 | 5.0 |
| Cannon | 4.3 | 3.5 | 0.22 | 1.9 | 5.0 |
| Chateau | 4.0 | 2.7 | 0.19 | 3.4 | 2.0 |
| Coventry | 3.7 | 3.0 | 0.14 | 0.7 | 4.3 |
| Eclipse | 3.9 | 3.2 | 0.19 | 8.7 | 5.0 |
| Fairfax | 4.3 | 3.2 | 0.20 | 1.0 | 4.9 |
| Georgetown | 5.7 | 2.8 | 0.22 | 1.9 | 5.0 |
| Gnome | 4.5 | 3.5 | 0.19 | 4.3 | 5.0 |
| Kelly | 4.8 | 4.1 | 0.18 | 3.1 | 4.4 |
| Marquis | 5.5 | 3.6 | 0.24 | 2.7 | 4.6 |
| Midnight | 3.8 | 2.6 | 0.19 | 1.1 | 5.0 |
| Nassau | 6.0 | 3.7 | 0.19 | 5.9 | 4.7 |
| Ram I | 3.5 | 3.1 | 0.19 | 1.0 | 4.8 |

TABLE 6-continued

Morphological Comparison of Flag Leaves of Ba 77-700 and Other Kentucky Bluegrass Varieties in the Greenhouse at Marysville, OH

| Variety | Length cm | Width mm | Thickness mm | Leaf Angle[1] | Leaf Curve[2] |
|---|---|---|---|---|---|
| Touchdown | 4.1 | 2.7 | 0.16 | 3.4 | 4.1 |
| Victa | 3.9 | 3.7 | 0.27 | 2.1 | 4.6 |
| Viva | 4.5 | 3.6 | 0.18 | 5.1 | 4.4 |
| LSD (.05) | 1.0 | 0.4 | 0.02 | 2.5 | 0.4 |

[1]Degrees from the stem
[2]Rating Scale: 1–9; 1 = curves up; 5 = no curve; 9 = curves down

TABLE 7

Morphological Comparison of Flag Leaves (Ligule Length, Hairs on the Leaf Margin and Ligule, and Sheath Color) of Ba 77-700 and Other Kentucky Bluegrass Varieties in the Greenhouse at Marysville, OH.

| | | Hairs[1] | | |
|---|---|---|---|---|
| Variety | Ligule Length (mm) | Leaf Margin | Ligule | Sheath Color[2] |
| Ba 77-700 | 1.3 | 1.5 | 2.3 | 1.8 |
| Abbey | 1.3 | 0.8 | 1.6 | 0.2 |
| Adelphi | 1.1 | 1.8 | 1.6 | 0.4 |
| Allure | 0.8 | 0.4 | 2.3 | 2.0 |
| America | 0.6 | 0.4 | 0.7 | 1.9 |
| Ascot | 1.5 | 0.6 | 0.7 | 0.9 |
| Baron | 1.2 | 1.0 | 3.8 | 2.6 |
| Bristol | 0.6 | 0.4 | 1.9 | 2.0 |
| Buckingham | 1.2 | 0.5 | 2.1 | 2.0 |
| Cannon | 1.3 | 0.4 | 3.6 | 1.5 |
| Chateau | 0.9 | 1.1 | 3.1 | 0.3 |
| Coventry | 0.9 | 0.8 | 1.7 | 2.0 |
| Eclipse | 1.1 | 1.0 | 1.0 | 0.2 |
| Fairfax | 1.0 | 0.1 | 2.5 | 1.7 |
| Georgetown | 0.6 | 0.6 | 2.0 | 2.0 |
| Gnome | 0.8 | 0.9 | 3.2 | 1.5 |
| Kelly | 1.5 | 1.1 | 2.5 | 2.2 |
| Marquis | 0.8 | 0.5 | 3.8 | 1.5 |
| Midnight | 0.4 | 0.4 | 0.3 | 2.0 |
| Nassua | 1.1 | 2.6 | 2.4 | 0.8 |
| Ram I | 0.7 | 0.5 | 1.3 | 2.0 |
| Touchdown | 1.1 | 1.0 | 1.0 | 7.7 |
| Victa | 1.3 | 1.0 | 0.8 | 0.5 |
| Viva | 1.5 | 0.4 | 2.2 | 0.5 |
| LSD (.05) | 0.17 | 0.47 | 0.7 | 0.76 |

[1]Rating Scale: 0–9; 0 = none; 9 = many
[2]Rating Scale: 0–9; 9 = dark purple

TABLE 8

Morphological Comparison of Peduncles, Culms, Node Numbers Per Culm and Internode Length of Ba 77-700 and Other Kentucky Bluegrass Varieties in the Greenhouse at Marysville, OH

| Variety | Peduncle Length cm | Peduncle Width mm | Culm Length cm | Nodes Per Culm | Top Internode Length (cm) |
|---|---|---|---|---|---|
| Ba 77-700 | 26.9 | 0.82 | 39.7 | 2.9 | 9.7 |
| Abbey | 23.2 | 0.65 | 41.3 | 4.1 | 11.0 |
| Adelphi | 24.5 | 0.66 | 40.0 | 4.0 | 10.4 |
| Allure | 17.9 | 0.61 | 28.0 | 3.1 | 7.7 |
| America | 16.2 | 0.62 | 31.8 | 3.1 | 11.0 |
| Ascot | 20.0 | 0.64 | 36.3 | 3.0 | 12.7 |
| Baron | 34.0 | 0.70 | 52.8 | 4.2 | 12.8 |
| Bristol | 22.9 | 0.73 | 43.5 | 4.0 | 12.6 |
| Buckingham | 24.7 | 0.71 | 44.9 | 3.7 | 13.4 |
| Cannon | 24.3 | 0.81 | 39.5 | 3.1 | 10.8 |
| Chateau | 20.7 | 0.61 | 38.9 | 4.4 | 9.9 |
| Coventry | 19.6 | 0.49 | 34.7 | 4.5 | 7.9 |

TABLE 8-continued

Morphological Comparison of Peduncles, Culms, Node Numbers Per Culm and Internode Length of Ba 77-700 and Other Kentucky Bluegrass Varieties in the Greenhouse at Marysville, OH

| Variety | Peduncle Length cm | Peduncle Width mm | Culm Length cm | Nodes Per Culm | Top Internode Length (cm) |
|---|---|---|---|---|---|
| Eclipse | 23.7 | 0.66 | 39.2 | 4.9 | 9.9 |
| Fairfax | 21.0 | 0.60 | 31.9 | 3.2 | 7.2 |
| Georgetown | 21.7 | 0.68 | 37.5 | 3.2 | 11.1 |
| Gnome | 19.4 | 0.84 | 35.3 | 3.1 | 9.2 |
| Kelly | 29.4 | 0.75 | 46.6 | 3.6 | 11.8 |
| Marquis | 27.1 | 0.83 | 34.1 | 3.4 | 7.8 |
| Midnight | 20.5 | 0.72 | 29.5 | 2.8 | 7.6 |
| Nassau | 25.0 | 0.66 | 36.0 | 3.9 | 7.4 |
| Ram I | 22.2 | 0.69 | 30.5 | 2.5 | 6.6 |
| Touchdown | 23.6 | 0.52 | 38.0 | 4.0 | 8.4 |
| Victa | 21.2 | 0.81 | 37.9 | 3.7 | 10.3 |
| Viva | 26.4 | 0.70 | 42.7 | 4.1 | 9.2 |
| LSD (.05) | 3.2 | 0.08 | 3.3 | 0.4 | 1.9 |

TABLE 9

Morphological Comparison of Vegetative Leaves (Length, Width, Thickness, Angle and Curvature) of Ba 77-700 and Other Kentucky Bluegrass Varieties in the Greenhouse at Marysville, OH

| | Length | Width | Thickness | Leaf | |
|---|---|---|---|---|---|
| Variety | cm | mm | mm | Angle[1] | Curve[2] |
| Ba 77-700 | 18.6 | 3.8 | 0.34 | 61.6 | 7.7 |
| Abbey | 20.7 | 3.6 | 0.28 | 51.3 | 7.4 |
| Adelphi | 19.4 | 3.7 | 0.28 | 67.0 | 4.6 |
| Allure | 18.1 | 3.5 | 0.30 | 53.0 | 6.2 |
| America | 21.4 | 3.1 | 0.32 | 66.0 | 6.4 |
| Ascot | 17.4 | 3.4 | 0.35 | 67.9 | 5.5 |
| Baron | 18.2 | 4.3 | 0.29 | 35.0 | 4.4 |
| Bristol | 18.2 | 3.7 | 0.32 | 65.5 | 6.9 |
| Buckingham | 18.9 | 4.5 | 0.36 | 50.9 | 5.0 |
| Cannon | 22.1 | 3.3 | 0.30 | 62.5 | 8.2 |
| Chateau | 23.1 | 3.3 | 0.33 | 39.7 | 5.4 |
| Coventry | 23.4 | 3.6 | 0.25 | 63.0 | 7.3 |
| Eclipse | 20.3 | 4.4 | 0.30 | 65.5 | 5.4 |
| Fairfax | 21.9 | 3.5 | 0.28 | 51.7 | 8.3 |
| Georgetown | 19.5 | 3.6 | 0.29 | 56.7 | 5.8 |
| Gnome | 18.2 | 2.9 | 0.29 | 43.2 | 6.6 |
| Kelly | 22.8 | 3.9 | 0.30 | 55.5 | 7.0 |
| Marquis | 19.7 | 3.7 | 0.38 | 46.4 | 7.8 |
| Midnight | 19.5 | 3.5 | 0.31 | 63.3 | 5.0 |
| Nassau | 16.3 | 3.7 | 0.29 | 63.2 | 4.9 |
| Ram I | 19.1 | 3.6 | 0.27 | 70.8 | 6.5 |
| Touchdown | 16.7 | 3.7 | 0.24 | 51.3 | 4.0 |
| Victa | 21.5 | 3.6 | 0.36 | 56.3 | 6.7 |
| Viva | 22.9 | 3.8 | 0.40 | 53.0 | 7.1 |
| LSD (.05) | 3.50 | 0.43 | 0.04 | 15.9 | 1.5 |

[1]Degrees from the stem
[2]Rating scale: 1–9; 1 = curves up; 5 = no curve; 9 = curves down

TABLE 10

Morphological Comparison of Vegetative Leaves (Ligule Length, Hairs on the Leaf Margin and Ligule, Sheath Roughness and Color) of Ba 77-700 and Other Kentucky Bluegrass Varieties in the Greenhouse at Marysville, OH

| | Ligule | Hairs[1] | | | |
|---|---|---|---|---|---|
| Variety | Length mm | Leaf Ligule | Leaf Margin | Sheath Roughness[2] | Sheath Color[3] |
| Ba 77-700 | 0.21 | 3.1 | 2.0 | 7.3 | 1.4 |
| Abbey | 0.32 | 4.4 | 2.8 | 7.7 | 0.0 |

TABLE 10-continued

Morphological Comparison of Vegetative Leaves (Ligule Length, Hairs on the Leaf Margin and Ligule, Sheath Roughness and Color) of Ba 77-700 and Other Kentucky Bluegrass Varieties in the Greenhouse at Marysville, OH

| Variety | Ligule Length mm | Hairs[1] Leaf Ligule | Hairs[1] Leaf Margin | Sheath Roughness[2] | Sheath Color[3] |
|---|---|---|---|---|---|
| Adelphi | 0.34 | 2.6 | 3.4 | 8.8 | 0.0 |
| Allure | 0.14 | 2.0 | 1.6 | 8.3 | 1.9 |
| America | 0.12 | 1.7 | 2.1 | 8.4 | 2.0 |
| Ascot | 0.22 | 1.5 | 2.0 | 8.8 | 0.2 |
| Baron | 0.33 | 4.6 | 3.6 | 7.4 | 0.4 |
| Bristol | 0.12 | 2.6 | 3.0 | 8.9 | 2.0 |
| Buckingham | 0.14 | 3.3 | 2.6 | 8.7 | 2.0 |
| Cannon | 0.16 | 3.2 | 0.7 | 8.2 | 2.0 |
| Chateau | 0.22 | 3.3 | 3.1 | 7.8 | 0.5 |
| Coventry | 0.32 | 3.1 | 2.4 | 8.1 | 0.3 |
| Eclipse | 0.38 | 2.8 | 2.6 | 9.0 | 0.2 |
| Fairfax | 0.14 | 2.7 | 1.4 | 8.1 | 1.7 |
| Georgetown | 0.14 | 2.5 | 2.4 | 8.5 | 2.0 |
| Gnome | 0.23 | 1.6 | 0.8 | 7.5 | 1.4 |
| Kelly | 0.34 | 4.6 | 2.4 | 8.8 | 0.0 |
| Marquis | 0.21 | 3.6 | 1.1 | 6.8 | 1.1 |
| Midnight | 0.10 | 1.3 | 1.6 | 7.7 | 2.0 |
| Nassau | 0.34 | 2.5 | 3.3 | 8.5 | 1.4 |
| Ram I | 0.09 | 1.8 | 2.0 | 7.7 | 2.0 |
| Touchdown | 0.29 | 1.4 | 1.3 | 7.9 | 8.0 |
| Victa | 0.26 | 2.3 | 1.7 | 7.9 | 0.1 |
| Viva | 0.23 | 5.2 | 4.2 | 8.5 | 0.0 |
| LSD (.05) | 0.04 | 0.79 | 0.70 | 0.89 | 0.57 |

[1]Rating Scale: 0–9; 0 = none; 9 = many
[2]Rating Scale: 1–9; 1 = rough; 9 = smooth
[3]Rating Scale: 0–9; 0 = no color; 9 = dark purple color Ba 77-700 has performed well as exhibited by medium to high turf quality ratings throughout the United Sates in comparison to other Kentucky Bluegrass varieties. Ba 77-700 has an attractive green color which can be maintained throughout the growing season.

With regard to a comparative analysis conducted for purposes of determining color of Ba 77-700 plants relative to other Kentucky Bluegrass varieties, readings were taken of the vegetative color of Ba 77-700 during mid-October while the turf was actively growing with adequate nutrient and water availability. The readings were taken in full sun with several actively growing leaves being compared, one at a time, utilizing color chips from the Munsell Book of Color as a reference. On this basis, the color of Ba 77-700 was determined to be 5 GY 4/6. During the same time period, the color of similar leaves of other Kentucky Bluegrass varieties were determined by the same procedure to be as follows: Victa — 5 GY 4/4; Bristol — 7.5 GY 4/4; Ascot — 5 GY 4/4; Midnight — 7.5 GY 4/4; Abbey — 5 GY 4/6; and Buckingham — 7.5 GY 4/4. However, it should be noted that the general apparent color of turf does not always correlate directly with the color of the individual actively growing leaves within the turf and that turf color varies with nutrient level and time of year with some varieties being darker or lighter green depending on such factors.

Ba 77-700 demonstrates good early spring greening and winter color in mild winter climates.

Comparisons of Ba 77-700 with other varieties for quality, genetic color, spring greening and winter color, living ground cover, leaf texture and seedling vigor are set forth hereinafter in Tables 11–17:

TABLE 11

A Comparison of Quality of Ba 77-700 and Other Kentucky Bluegrass Varieties at Five (5) Test Locations in the U.S.

| Variety | Locations: Fort Collins, Co | Lexington, Kentucky | Adelphia, NJ | Kingston, RI | Beltsville, MD |
|---|---|---|---|---|---|
| Ba 77-700 | 6.3 | 6.5 | 4.8 | 5.7 | 6.5 |
| A-34 | 5.2 | 5.8 | 5.2 | 5.6 | 6.7 |
| Abbey | 6.3 | 6.2 | 4.7 | 5.7 | 6.3 |
| Able I | 6.3 | 6.9 | 6.2 | 5.8 | 5.9 |
| Allure | 5.9 | 5.4 | 4.9 | 5.3 | 6.5 |
| Ascot | 6.7 | 6.5 | 5.9 | 5.7 | 6.0 |
| Banff | 6.1 | 5.8 | 5.6 | 5.0 | 5.2 |
| Baron | 5.3 | 6.0 | 4.6 | 5.7 | 6.5 |
| Buckingham | 5.6 | 5.9 | 5.0 | 4.6 | 5.3 |
| Challenger | 6.1 | 6.6 | 5.4 | 5.2 | 6.6 |
| Cannon | 6.1 | 6.0 | 4.9 | 5.4 | 6.4 |
| Classic | 5.8 | 5.8 | 5.5 | 5.4 | 5.6 |
| Coventry | 6.1 | 5.6 | 4.7 | 5.0 | 6.6 |
| Eclipse | 6.6 | 6.5 | 6.3 | 6.1 | 6.8 |
| Estate | 5.8 | 4.8 | 5.0 | 5.2 | 6.3 |
| Fairfax | 5.9 | 5.1 | 5.1 | 5.3 | 6.8 |
| Georgetown | 5.8 | 5.9 | 5.1 | 5.3 | 5.3 |
| Glade | 6.1 | 6.4 | 5.1 | 5.8 | 6.7 |
| Gnome | 5.9 | 6.2 | 4.6 | 5.4 | 6.5 |
| Haga | 5.6 | 6.0 | 4.8 | 5.2 | 6.0 |
| Kelly | 5.9 | 6.1 | 4.5 | 5.2 | 6.4 |
| Kenblue | 3.7 | 5.0 | 2.4 | 4.9 | 5.4 |
| Liberty | 6.2 | 5.6 | 5.7 | 5.3 | 5.9 |
| Marquis | 6.2 | 6.9 | 4.5 | 5.6 | 6.4 |
| Merion | 5.1 | 5.9 | 4.0 | 5.4 | 5.7 |
| Merit | 6.1 | 6.5 | 4.2 | 5.7 | 6.3 |
| Midnight | 7.1 | 8.2 | 6.7 | 5.1 | 7.5 |
| Monopoly | 4.7 | 5.5 | 5.0 | 5.5 | 5.9 |
| Nassau | 5.8 | 6.5 | 4.7 | 5.2 | 4.9 |
| Ram I | 6.1 | 5.0 | 4.6 | 5.7 | 6.9 |
| South Dakota | 4.1 | 4.3 | 2.3 | 4.6 | 5.2 |
| Touchdown | 6.4 | 5.8 | 5.3 | 5.2 | 6.4 |
| Viva | 6.1 | 6.3 | 4.2 | 5.9 | 6.3 |
| LSD (.05) | 0.7 | 1.0 | 0.7 | 0.7 | 0.8 |

Quality Rating Scale: 1–9; 9 = ideal turf

TABLE 12

A Comparison of Genetic Color of Ba 77-700 and Other Kentucky Bluegrass Varieties in Three Test (A–C) Conducted at Ten (10) Locations in the US

| Variety | TESTS (Annual Means) A | B | C |
|---|---|---|---|
| Ba 77-700 | 5.7 | 5.5 | 5.8 |
| A-34 | 5.0 | 5.4 | 4.6 |
| Abbey | 5.6 | 5.9 | 5.8 |
| Able I | 6.6 | 6.8 | 6.8 |
| Allure | 5.7 | 5.2 | 5.6 |
| Ascot | 6.9 | 6.8 | 7.2 |
| Banff | 5.1 | 6.0 | 5.5 |
| Baron | 6.0 | 6.0 | 5.9 |
| Buckingham | 7.0 | 7.2 | 7.2 |
| Cannon | 6.0 | 5.7 | 6.4 |
| Challenger | 6.0 | 6.2 | 5.9 |
| Classic | 5.2 | 5.9 | 5.2 |
| Coventry | 5.9 | 5.6 | 5.8 |
| Eclipse | 6.3 | 6.6 | 6.4 |
| Estate | 5.8 | 5.3 | 5.3 |
| Fairfax | 6.0 | 5.4 | 5.4 |
| Georgetown | 5.2 | 6.1 | 5.3 |
| Glade | 6.7 | 6.3 | 6.7 |
| Gnome | 6.0 | 6.1 | 5.8 |
| Haga | 5.1 | 5.8 | 5.3 |
| Kelly | 5.6 | 5.7 | 6.1 |

TABLE 12-continued

A Comparison of Genetic Color of Ba 77-700 and Other Kentucky Bluegrass Varieties in Three Test (A–C) Conducted at Ten (10) Locations in the US

| | TESTS (Annual Means) | | |
|---|---|---|---|
| Variety | A | B | C |
| Kenblue | 4.6 | 5.0 | 5.3 |
| Liberty | 5.9 | 4.0 | 6.1 |
| Marquis | 6.1 | 6.1 | 6.4 |
| Merion | 5.7 | 5.8 | 5.4 |
| Merit | 5.7 | 5.7 | 6.2 |
| Midnight | 7.1 | 7.3 | 7.7 |
| Monopoly | 4.8 | 4.9 | 4.8 |
| Nassau | 6.0 | 6.6 | 6.5 |
| Ram I | 6.7 | 5.9 | 6.6 |
| South Dakota | 4.5 | 4.8 | 4.7 |
| Touchdown | 5.5 | 5.5 | 6.3 |
| Viva | 5.5 | 5.5 | 5.9 |
| LSD (.05) | 0.5 | 0.4 | 0.7 |

Rating Scale: 1–9; 9 = dark green.

TABLE 13

A Comparison of Spring Greenup of Ba 77-700 and Other Kentucky Bluegrass Varieties at Martinsville, New Jersey

| Variety | Spring Greenup |
|---|---|
| Ba 77-700 | 6.0 |
| A-34 | 6.0 |
| Abbey | 5.3 |
| Able I | 6.3 |
| Allure | 4.3 |
| Ascot | 3.7 |
| Banff | 3.7 |
| Baron | 4.0 |
| Buckingham | 5.0 |
| Cannon | 5.3 |
| Challenger | 5.3 |
| Classic | 5.3 |
| Coventry | 4.3 |
| Eclipse | 4.7 |
| Estate | 5.0 |
| Fairfax | 4.0 |
| Georgetown | 4.7 |
| Glade | 4.0 |
| Gnome | 4.7 |
| Haga | 5.7 |
| Kelly | 4.0 |
| Kenblue | 3.0 |
| Liberty | 4.7 |
| Marquis | 5.0 |
| Merion | 3.7 |
| Merit | 4.0 |
| Midnight | 2.7 |
| Monopoly | 4.7 |
| Nassau | 5.3 |
| Ram I | 5.0 |
| South Dakota | 4.0 |
| Touchdown | 5.7 |
| Viva | 5.0 |
| LSD (.05) | 1.8 |

Spring Greenup Rating Scale: 1–9; 9 = Completely green

TABLE 14

A Comparison of Winter Color of Ba 77-700 and Other Kentucky Bluegrass Varieties in Two Tests (A–B).

| Variety | A[1/] | B[2/] |
|---|---|---|
| Ba 77-700 | 5.0 | 5.0 |
| A-34 | 6.7 | 2.0 |
| Abbey | 1.7 | 6.3 |
| Able I | 6.3 | 3.3 |
| Allure | 6.0 | 6.3 |
| Ascot | 4.7 | 4.3 |
| Banff | 9.0 | 3.7 |
| Baron | 2.3 | 5.7 |
| Buckingham | 5.3 | 6.3 |
| Cannon | 2.3 | 6.0 |
| Challenger | 7.3 | 4.3 |
| Classic | 9.0 | 3.3 |
| Coventry | 7.0 | 3.7 |
| Eclipse | 4.7 | 3.7 |
| Estate | 5.7 | 5.0 |
| Fairfax | 6.0 | 4.5 |
| Georgetown | 8.0 | 3.3 |
| Glade | 1.7 | 3.7 |
| Gnome | 1.0 | 5.7 |
| Haga | 9.0 | 3.0 |
| Kelly | 2.3 | 5.7 |
| Kenblue | 1.3 | 3.0 |
| Liberty | 7.3 | 3.3 |
| Marquis | 2.0 | 5.0 |
| Merion | 6.7 | 3.3 |
| Merit | 3.7 | 6.0 |
| Midnight | 3.0 | 1.7 |
| Monopoly | 4.3 | 2.7 |
| Nassau | 7.7 | 5.0 |
| Ram I | 1.7 | 3.7 |
| South Dakota | 2.3 | 4.0 |
| Touchdown | 3.0 | 2.3 |
| Viva | 2.3 | 4.0 |
| LSD (.05) | 1.9 | 2.1 |

Winter Color Rating Scale: 1–9; 9 = Complete color retention
[1/]Location of Test A: North Brunswick, NJ
[2/]Location of Test B: Post Falls, ID

TABLE 15

A Comparison of Percent Living Ground Cover in the Fall of Ba 77-700 and Other Kentucky Bluegrass Varieties at Haymarket, VA

| Variety | % Ground Cover |
|---|---|
| Ba 77-700 | 70.0 |
| A-34 | 30.0 |
| Abbey | 68.3 |
| Able I | 28.3 |
| Allure | 83.3 |
| Ascot | 11.7 |
| Banff | 21.7 |
| Baron | 71.0 |
| Buckingham | 30.0 |
| Cannon | 75.0 |
| Challenger | 60.0 |
| Classic | 31.7 |
| Coventry | 65.0 |
| Eclipse | 48.3 |
| Estate | 71.7 |
| Fairfax | 70.0 |
| Georgetown | 33.3 |
| Glade | 68.3 |
| Gnome | 70.0 |
| Haga | 53.3 |
| Kelly | 83.3 |
| Kenblue | 94.3 |
| Liberty | 33.3 |
| Marquis | 88.3 |
| Merion | 81.7 |

TABLE 15-continued

A Comparison of Percent Living Ground Cover in the Fall of Ba 77-700 and Other Kentucky Bluegrass Varieties at Haymarket, VA

| Variety | % Ground Cover |
|---|---|
| Merit | 71.7 |
| Midnight | 38.3 |
| Monopoly | 85.0 |
| Nassau | 36.7 |
| Ram I | 65.0 |
| South Dakota | 86.0 |
| Touchdown | 33.3 |
| Viva | 85.0 |
| LSD (.05) | 29.9 |

TABLE 16

A Comparison of Leaf Texture of Ba 77-700 and Other Kentucky Bluegrass Varieties in Two Tests (A–B)

| Variety | A[1/] | B[2/] |
|---|---|---|
| Ba 77-700 | 4.0 | 4.0 |
| Abbey | 5.0 | 4.3 |
| Able I | 5.7 | 6.3 |
| Allure | 4.3 | 4.0 |
| Ascot | 5.3 | 6.0 |
| A-34 | 4.3 | 5.2 |
| Banff | 5.3 | 5.2 |
| Baron | 5.0 | 4.2 |
| Buckingham | 4.0 | 3.7 |
| Cannon | 4.0 | 4.0 |
| Challenger | 5.0 | 4.5 |
| Classic | 5.3 | 5.3 |
| Coventry | 5.0 | 4.2 |
| Eclipse | 5.7 | 5.7 |
| Estate | 4.3 | 3.8 |
| Fairfax | 4.7 | 4.0 |
| Georgetown | 6.0 | 4.8 |
| Glade | 5.0 | 4.6 |
| Gnome | 5.3 | 4.2 |
| Haga | 5.7 | 5.2 |
| Kelly | 4.3 | 4.0 |
| Kenblue | 6.0 | 5.8 |
| Liberty | 5.0 | 4.7 |
| Marquis | 4.3 | 4.2 |
| Merion | 4.0 | 4.2 |
| Merit | 4.7 | 4.0 |
| Midnight | 6.7 | 6.0 |
| Monopoly | 5.0 | 4.5 |
| Nassau | 5.0 | 4.3 |
| Ram I | 5.0 | 4.8 |
| South Dakota | 3.7 | 4.8 |
| Touchdown | 5.3 | 5.8 |
| Viva | 4.3 | 4.0 |
| LSD (.05) | 0.9 | 0.8 |

Leaf Texture Rating Scale: 1–9; 9 = very fine
[1/]Test Location: Martinsville, NJ
[2/]Test Location: Martinsville, NJ; and pooled data from Halsey, Hubbard and Gervais, OR

TABLE 17

A Comparison of Seeding Vigor of Ba 77-700 and Other Kentucky Bluegrass Varieties at Six Locations in The U.S. and Canada[1/]

| Variety | Seedling Vigor (Mean) |
|---|---|
| Ba 77-700 | 6.8 |
| A-34 | 6.0 |
| Abbey | 6.4 |
| Able I | 6.3 |

TABLE 17-continued

A Comparison of Seeding Vigor of Ba 77-700 and Other Kentucky Bluegrass Varieties at Six Locations in The U.S. and Canada[1/]

| Variety | Seedling Vigor (Mean) |
|---|---|
| Allure | 6.2 |
| Ascot | 6.2 |
| Banff | 7.7 |
| Baron | 6.7 |
| Buckingham | 5.3 |
| Cannon | 6.3 |
| Challenger | 5.6 |
| Classic | 7.1 |
| Coventry | 6.1 |
| Eclipse | 6.1 |
| Estate | 6.1 |
| Fairfax | 6.4 |
| Georgetown | 7.0 |
| Glade | 6.7 |
| Gnome | 6.3 |
| Haga | 7.1 |
| Kelly | 6.6 |
| Kenblue | 7.4 |
| Liberty | 6.4 |
| Marquis | 6.3 |
| Merion | 2.6 |
| Merit | 6.4 |
| Midnight | 5.4 |
| Monopoly | 7.1 |
| Nassau | 6.4 |
| Ram I | 6.5 |
| South Dakota | 6.7 |
| Touchdown | 5.8 |
| Viva | 6.3 |
| LSD (.05) | 0.7 |

Rating Scale: 1–9; 9 = Maximum vigor.
[1/]Locations: Fort Collins, CO; Post Falls, ID; North Brunswick, NJ; Adelphia, NJ; Richmond Hills, Ontario; pooled data from Halsey, Hubbard and Gervais, OR.

Turf diseases are one of the major causes of inconsistent and poor turf performance. Ba 77-700 has been found to have a medium to high level of resistance to leaf spot and melting out caused by *Drechslera poae* (formerly called *Helminthosporium vagans*). Ba 77-700 furthermore has been found to have a medium to high level of resistance to dollar spot caused by *Sclerotinia homoecarpa* and to several rust diseases caused by Puccinia spp. as well as to necrotic ring spot caused by *Leptosphaeria korrae*.

Comparisons of disease incidence of Ba 77-700 as compared with other Kentucky Bluegrass varieties in regard to leaf spot, dollar spot, rusts and necrotic ring spot are presented in Tables 18–23 as follows:

TABLE 18

A Comparison of Leaf Spot Incidence in Ba 77-700 and Other Kentucky Bluegrass Varieties in Two Tests (A-B) Conducted at Four Locations in the U.S.

| Variety | Means | |
|---|---|---|
| | Test A[1/] | Test B[2/] |
| Ba77-700 | 7.2 | 5.7 |
| A-34 | 7.2 | 5.4 |
| Abbey | 7.8 | 5.1 |
| Able I | 7.8 | 7.1 |
| Allure | 7.7 | 5.8 |
| Ascot | 8.1 | 7.4 |
| Banff | 4.8 | 5.9 |
| Baron | 7.1 | 5.4 |

TABLE 18-continued

A Comparison of Leaf Spot Incidence in Ba 77-700 and Other Kentucky Bluegrass Varieties in Two Tests (A-B) Conducted at Four Locations in the U.S.

| Variety | Means | |
|---|---|---|
| | Test A[1/] | Test B[2/] |
| Buckingham | 8.3 | 6.8 |
| Cannon | 8.0 | 5.8 |
| Challenger | 8.0 | 6.9 |
| Classic | 7.8 | 5.4 |
| Coventry | 6.8 | 5.8 |
| Eclipse | 7.9 | 7.4 |
| Estate | 7.9 | 5.9 |
| Fairfax | 6.6 | 4.9 |
| Georgetown | 8.0 | 6.3 |
| Glade | 4.8 | 4.8 |
| Gnome | 7.6 | 5.7 |
| Haga | 7.2 | 5.9 |
| Kelly | 7.2 | 5.1 |
| Kenblue | 1.2 | 1.8 |
| Liberty | 8.1 | 6.8 |
| Marquis | 7.4 | 5.6 |
| Merion | 8.0 | 7.3 |
| Merit | 7.4 | 5.4 |
| Midnight | 8.1 | 6.6 |
| Monopoly | 7.1 | 5.2 |
| Nassau | 8.2 | 6.2 |
| Ram I | 3.4 | 4.9 |
| South Dakota | 2.2 | 1.8 |
| Touchdown | 7.4 | 6.3 |
| Viva | 7.4 | 5.1 |
| LSD (.05) | 0.9 | 0.7 |

Rating Scale: 1–9; 9 = no disease
[1/]Locations: Post Falls, ID; North Brunswick and Adelphia, NJ
[2/]Locations: Post Falls, ID; North Brunswick and Adelphia, NJ; Marysville, OH

TABLE 19

A Comparison of Dollar Spot Disease Incidence of Ba 77-700 and Other Kentucky Bluegrass Varieties in Two Tests Conducted in the U.S.

| Variety | Means | |
|---|---|---|
| | Test A[1/] | Test B[2/] |
| Ba 77-700 | 7.0 | 7.0 |
| A-34 | 6.7 | 6.0 |
| Abbey | 6.8 | 6.3 |
| Able I | 6.8 | 6.1 |
| Allure | 6.4 | 5.3 |
| Ascot | 7.8 | 7.0 |
| Banff | 6.4 | 6.2 |
| Baron | 6.9 | 6.8 |
| Buckingham | 7.9 | 4.8 |
| Canon | 6.6 | 6.4 |
| Challenger | 6.4 | 4.7 |
| Classic | 7.4 | 6.3 |
| Coventry | 5.9 | 5.9 |
| Eclipse | 7.5 | 7.2 |
| Estate | 5.3 | 5.6 |
| Fairfax | 5.8 | 6.0 |
| Georgetown | 6.9 | 6.1 |
| Glade | 7.0 | 6.4 |
| Gnome | 6.7 | 6.1 |
| Haga | 6.3 | 6.2 |
| Kelly | 7.3 | 6.3 |
| Kenblue | 6.8 | 6.8 |
| Liberty | 7.3 | 6.8 |
| Marquis | 6.8 | 6.7 |
| Merion | 6.9 | 6.1 |
| Merit | 6.8 | 6.7 |
| Midnight | 8.0 | 6.6 |
| Monopoly | 7.1 | 6.7 |

TABLE 19-continued

A Comparison of Dollar Spot Disease Incidence of Ba 77-700 and Other Kentucky Bluegrass Varieties in Two Tests Conducted in the U.S.

| Variety | Means | |
|---|---|---|
| | Test A[1/] | Test B[2/] |
| Nassau | 7.4 | 6.7 |
| Ram I | 6.0 | 4.9 |
| South Dakota | 7.3 | 5.8 |
| Touchdown | 6.8 | 6.1 |
| Viva | 7.1 | 6.2 |
| LSD (.05) | 1.1 | 0.8 |

Rating Scale: 1–9; 9 = no disease.
[1/]Locations: Urbana, IL; Adelphia, NJ; Kingston, RI; Haymarket, VA
[2/]Locations: Urbana, IL; Silver Spring, MD; Kingston, RI

TABLE 20

A Comparison of Stem Rust Disease Incidence in Ba 77-700 and Other Kentucky Bluegrass Varieties at Adelphia, NJ

| Variety | Stem Rust |
|---|---|
| Ba 77-700 | 7.3 |
| A-34 | 4.3 |
| Abbey | 7.0 |
| Able I | 3.3 |
| Allure | 6.3 |
| Ascot | 7.3 |
| Banff | 7.7 |
| Baron | 7.0 |
| Buckingham | 5.7 |
| Cannon | 7.3 |
| Challenger | 4.0 |
| Classic | 8.0 |
| Coventry | 6.7 |
| Eclipse | 4.0 |
| Estate | 6.3 |
| Fairfax | 6.3 |
| Georgetown | 8.7 |
| Glade | 7.7 |
| Gnome | 7.0 |
| Haga | 8.0 |
| Kelly | 8.0 |
| Kenblue | 5.7 |
| Liberty | 7.7 |
| Marquis | 6.7 |
| Merion | 1.0 |
| Merit | 6.3 |
| Midnight | 8.0 |
| Monopoly | 6.3 |
| Nassau | 8.0 |
| Ram I | 8.0 |
| South Dakota | 4.3 |
| Touchdown | 2.3 |
| Viva | 6.7 |
| LSD (.05) | 1.4 |

Rating Scale: 1–9; 9 = no disease

TABLE 21

A Comparison of Leaf Rust Disease Incidence in Ba 77-700 and Other Kentucky Bluegrass Varieties at Kingston, R.I.

| Variety | Leaf Rust |
|---|---|
| Ba 77-700 | 8.0 |
| A-34 | 6.0 |
| Abbey | 6.3 |
| Able I | 7.0 |
| Allure | 6.0 |
| Ascot | 6.0 |
| Banff | 7.0 |

TABLE 21-continued

A Comparison of Leaf Rust Disease Incidence in Ba 77-700 and Other Kentucky Bluegrass Varieties at Kingston, R.I.

| Variety | Leaf Rust |
|---|---|
| Baron | 8.3 |
| Buckingham | 6.7 |
| Cannon | 6.3 |
| Challenger | 5.7 |
| Classic | 8.7 |
| Coventry | 7.0 |
| Eclipse | 5.7 |
| Estate | 6.3 |
| Fairfax | 6.0 |
| Georgetown | 7.7 |
| Glade | 7.0 |
| Gnome | 6.7 |
| Haga | 7.0 |
| Kelly | 5.0 |
| Kenblue | 6.7 |
| Liberty | 7.3 |
| Marquis | 6.3 |
| Merion | 2.3 |
| Merit | 6.0 |
| Midnight | 6.0 |
| Monopoly | 5.3 |
| Nassau | 7.0 |
| Ram I | 6.7 |
| South Dakota | 6.7 |
| Touchdown | 3.7 |
| Viva | 5.7 |
| LSD (.05) | 2.4 |

Rating Scale: 1–9; 9 = no disease.

TABLE 22

A Comparison of Stripe Rust Disease Incidence in Ba 77-700 and Other Kentucky Bluegrass Varieties in Tests Conducted at Three Locations[1/]

| Variety | Stripe Rust |
|---|---|
| Ba 77-700 | 5.0 |
| A-34 | 5.0 |
| Abbey | 4.3 |
| Able I | 6.0 |
| Allure | 4.3 |
| Ascot | 6.0 |
| Banff | 6.0 |
| Baron | 6.0 |
| Buckingham | 5.7 |
| Cannon | 4.7 |
| Challenger | 5.3 |
| Classic | 6.3 |
| Coventry | 5.0 |
| Eclipse | 6.0 |
| Estate | 5.7 |
| Fairfax | 5.7 |
| Georgetown | 6.3 |
| Glade | 3.0 |
| Gnome | 4.7 |
| Haga | 6.3 |
| Kelly | 5.0 |
| Kenblue | 3.3 |
| Liberty | 5.3 |
| Marquis | 5.3 |
| Merion | 3.7 |
| Merit | 5.0 |
| Midnight | 4.7 |
| Monopoly | 5.3 |
| Nassau | 5.3 |
| Ram I | 6.0 |
| South Dakota | 4.0 |

TABLE 22-continued

A Comparison of Stripe Rust Disease Incidence in Ba 77-700 and Other Kentucky Bluegrass Varieties in Tests Conducted at Three Locations[1/]

| Variety | Stripe Rust |
|---|---|
| Touchdown | 3.0 |
| Viva | 5.0 |
| LSD (.05) | 1.2 |

Rating Scale: 1–9; 9 = no disease

[1/]Pooled data from Halsey, Hubbard and Gervais, Oregon.

TABLE 23

A Comparison of Necrotic Ring Spot Incidence in Ba 77-700 and Other Kentucky Bluegrass Varieties at Post Falls, ID

| Variety | Nocrotic Ring Spot |
|---|---|
| Ba 77-700 | 7.3 |
| A-34 | 6.0 |
| Abbey | 7.3 |
| Able I | 7.3 |
| Allure | 3.3 |
| Ascot | 8.0 |
| Banff | 7.7 |
| Baron | 7.3 |
| Buckingham | 8.7 |
| Cannon | 7.0 |
| Challenger | 8.3 |
| Classic | 6.7 |
| Coventry | 5.0 |
| Eclipse | 7.7 |
| Estate | 4.7 |
| Fairfax | 3.5 |
| Georgetown | 7.7 |
| Glade | 8.3 |
| Gnome | 7.3 |
| Haga | 7.7 |
| Kelly | 7.3 |
| Kenblue | 5.7 |
| Liberty | 6.7 |
| Marquis | 7.7 |
| Merion | 5.3 |
| Merit | 7.7 |
| Midnight | 8.3 |
| Monopoly | 6.7 |
| Nassau | 7.7 |
| Ram I | 7.0 |
| South Dakota | 7.0 |
| Touchdown | 6.3 |
| Viva | 7.7 |
| LSD (.05) | 1.9 |

Rating Scale: 1–9; 9 = no disease

Ba 77-700 has shown good drought tolerance and seed yielding capability. Comparisons for drought tolerance and seed yields of Ba 77-700 with other Kentucky Bluegrasses are presented in Tables 24-26.

TABLE 24

A Comparison of Drought Tolerance of Ba 77-700 and Other Kentucky Bluegrass Varieties at Haymarket, VA

| Variety | Drought Tolerance |
|---|---|
| Ba77-700 | 5.3 |
| A-34 | 3.0 |
| Abbey | 4.3 |
| Able I | 3.3 |
| Allure | 4.0 |
| Ascot | 4.0 |
| Banff | 3.3 |

TABLE 24-continued

A Comparison of Drought Tolerance of Ba 77-700 and Other Kentucky Bluegrass Varieties at Haymarket, VA

| Variety | Drought Tolerance |
|---|---|
| Baron | 4.0 |
| Buckingham | 4.0 |
| Cannon | 4.0 |
| Challenger | 3.3 |
| Classic | 3.7 |
| Coventry | 3.7 |
| Eclipse | 4.3 |
| Estate | 4.3 |
| Fairfax | 4.3 |
| Georgetown | 3.7 |
| Glade | 5.0 |
| Gnome | 3.7 |
| Haga | 3.0 |
| Kelly | 4.0 |
| Kenblue | 4.0 |
| Liberty | 3.0 |
| Marquis | 4.7 |
| Merion | 3.7 |
| Merit | 4.7 |
| Midnight | 3.7 |
| Monopoly | 4.0 |
| Nassau | 3.3 |
| Ram I | 4.3 |
| South Dakota | 4.0 |
| Touchdown | 4.0 |
| Viva | 4.7 |
| LSD (.05) | 1.1 |

Dormancy Rating Scale: 1–9; 9 = no dormancy.

TABLE 25

A Comparison of Drought Recovery of Ba 77-700 and Other Kentucky Bluegrass Varieties in Two Tests (A-B)

| Variety | Test A[1/] | Test B[2/] |
|---|---|---|
| Ba 77-700 | 4.8 | 3.0 |
| A-34 | 3.3 | 1.0 |
| Abbey | 4.5 | 2.7 |
| Able I | 4.3 | 1.3 |
| Allure | 4.7 | 5.3 |
| Ascot | 3.2 | 1.0 |
| Banff | 3.5 | 1.0 |
| Baron | 5.5 | 4.0 |
| Buckingham | 2.8 | 2.0 |
| Cannon | 4.3 | 2.7 |
| Challenger | 3.5 | 3.3 |
| Classic | 4.2 | 1.3 |
| Coventry | 4.7 | 2.7 |
| Eclipse | 3.3 | 2.0 |
| Estate | 5.5 | 3.0 |
| Fairfax | 5.0 | 3.0 |
| Georgetown | 3.5 | 1.0 |
| Glade | 4.2 | 2.3 |
| Gnome | 4.8 | 2.7 |

TABLE 25-continued

A Comparison of Drought Recovery of Ba 77-700 and Other Kentucky Bluegrass Varieties in Two Tests (A-B)

| Variety | Test A[1/] | Test B[2/] |
|---|---|---|
| Haga | 4.0 | 2.7 |
| Kelly | 4.5 | 4.3 |
| Kenblue | 4.8 | 4.7 |
| Liberty | 4.2 | 1.7 |
| Marquis | 4.2 | 4.7 |
| Merion | 3.5 | 4.3 |
| Merit | 5.7 | 3.7 |
| Midnight | 4.5 | 1.0 |
| Monopoly | 4.7 | 5.3 |
| Nassau | 5.0 | 2.3 |
| Ram I | 4.3 | 3.0 |
| South Dakota | 3.7 | 3.3 |
| Touchdown | 4.3 | 1.3 |
| Viva | 4.8 | 3.7 |
| LSD (.05) | 1.2 | 1.8 |

Drought Recovery Rating Scale: 1–9; 9 = Complete recovery
[1/]Locations: Carbondale, IL; and pooled data from Halsey, Hubbard and Gervais, OR
[2/]Locations: Haymarket, VA

TABLE 26

A Comparison of Seed Yield in Pounds Per Acre of Ba 77-700 and Other Kentucky Bluegrass Varieties in Two (2) Tests

| Variety | Test A[1/] | Test B[2/] |
|---|---|---|
| Ba 77-700 | 1495 | 1569 |
| Abbey | — | 1549 |
| Allure | 859 | — |
| Bristol | 862 | — |
| Buckingham | 865 | 748 |
| Cannon | — | 1551 |
| Coventry | — | 1046 |
| Fairfax | — | 1159 |
| Victa | 1342 | — |
| Viva | 1382 | 1612 |
| LSD (.05) | 216 | 160 |

[1/]Test Location: Gervais, OR
[2/]Test Location: La Grande, OR

What is claimed is:

1. A variety of Kentucky Bluegrass plant, substantially as shown and described, characterized by a medium to high level of resistance to leaf spot, dollar spot, rusts, and necrotic ring spot; an attractive green color throughout the growing season; good early spring greening; medium to high quality turf formation under a wide variety of environmental conditions; a moderately wide blade; and a high level of seed yielding capacity.

* * * * *